US005446019A

United States Patent [19]

Ely et al.

[11] Patent Number: 5,446,019

[45] Date of Patent: Aug. 29, 1995

[54] ***BACILLUS THURINGIENSIS* TOXIN WITH ACTIVITY AGAINST DIABROTICA SPECIES**

[75] Inventors: Susan Ely, Ithaca, N.Y.; Janet M. Tippett, Ames, Iowa

[73] Assignee: Zeneca Limited, London, England

[21] Appl. No.: 178,554

[22] Filed: Jan. 6, 1994

[30] Foreign Application Priority Data

Jan. 6, 1993 [GB] United Kingdom ................. 9300124

[51] Int. Cl.[6] ............................................ A01N 37/18

[52] U.S. Cl. .................................... 514/2; 424/93.461

[58] Field of Search ....................... 514/2, 15; 424/932; 435/252.5, 252.1, 69.1, 832, 252.31

[56] References Cited

U.S. PATENT DOCUMENTS 5,208,017 5/1993 Bradfisch et al. ................... 435/242

5,262,323 11/1993 Baird et al. ....................... 435/252.5

5,264,364 11/1993 Donovan et al. ................ 435/252.5

OTHER PUBLICATIONS

Murray, et al (1991) Plant Molecular Biology 16: 1035, Abstract.

Thorne, et al (Jun. 1986) Journal of Bacteriology 166(3):801-811.

*Primary Examiner*—Che S. Chereskin

*Attorney, Agent, or Firm*—Cushman Darby & Cushman

[57] ABSTRACT

The novel strain JHCC 5767 of *Bacillus thuringiensis*, and insecticidal compositions containing insecticidal protein(s) produced by said strain are provided. A process for protecting plants from insects of the genus Diabrotica by exposing larvae to insecticidal protein produced by said strain is also provided. Novel genes for insecticidal proteins may be isolated from strain JHCC 5767.

3 Claims, No Drawings

*BACILLUS THURINGIENSIS* TOXIN WITH ACTIVITY AGAINST DIABROTICA SPECIES

The present invention relates to a novel bacterial strain, and in particular to a novel strain of the bacterium *Bacillus thuringiensis* and uses therefor.

The organism *Bacillus thuringiensis* produces a crystal-associated protein endotoxin which kills insect larvae upon ingestion. It is not however toxic to mammals. It is thus very useful as an agricultural insecticide, in particular against Lepidoptera, Coleoptera and Diptera. Strains of *Bacillus thuringiensis* (in particular, strain HD-1) have been used as agricultural insecticides for a number of decades.

The most extensively characterised strain of *Bacillus thuringiensis* active against coleopteran pests is *Bacillus thuringiensis* subsp. *tenebrionis,* as deposited in the German Collection of Microorganisms (Deutsche Sammlung von Microorganismen) under the reference DSM 2803. We have now discovered a novel strain of *Bacillus thuringiensis* having some properties similar to *Bacillus thuringiensis* subsp. *tenebrionis,* but distinguished therefrom by specific insecticidal activity against coleopteran larvae of the genus Diabrotica.

According to the present invention we provide the novel strain JHCC 5767 of *Bacillus thuringiensis,* deposited on 21 Dec. 1992 under the terms of the Budapest Treaty at the National Collections of Industrial and Marine Bacteria (23 St Machar Drive, Aberdeen, Scotland, AB2 1RY) under the accession number NCIMB 40533.

*B. thuringiensis* strain JHCC 5767 is useful as an insecticidal agent to combat insects of the genus Diabrotica.

*B thuringiensis* strain JHCC 5767 was a soil isolate from Tama Country, Iowa, USA. In colonial morphology, strain JHCC 5767 is generally similar to other strains of *Bacillus thuringiensis.* The biochemical properties of strain JHCC 5767 are also generally similar to those of known *Bacillus thuringiensis* strains, as shown Table 1.

TABLE 1

Biochemical markers

| Reagent | *B thuringiensis* strain: HD-1 | DSM 2803 | JHCC 5767 |
|---|---|---|---|
| D-mannose | − | + | + |
| Esculine | + | − | − |
| Salicine | + | − | − |
| Cellobiose | + | − | − |
| Sucrose | − | + | + |
| 6Br2NGP* | + | − | ND |
| Urease | + | − | − |
| $NO_2$—*NO3* | + | − | + |

*6-Br-2-Naphthyl-BD-glucopyranoside;
ND = not determined.

*B thuringiensis* strains JHCC 5767 and DSM 2803 both contain the well-described delta-endotoxin cryIIIA gene known to encode a protein insecticidal to various coleopteran larvae, for example larvae of the Colorado potato beetle, *Leptinotarsa decimlineata.* Published reports (Macintosh S et al, 1990, J Invert Pathol, 56:258-266) and data shown in Table 3 (Example 7) indicate that the 66 kDalton CryIIIA protein is not, however, toxic to Diabrotica species larvae.

We now provide novel insecticidal material which may be derived from *Bacillus thuringiensis* strain 5767, but which does not contain the CryIIIA protein or proteins immunologically related to CryIIIA. Such material is active against the larvae of Diabrotica species, including Western Corn Rootworm.

The biochemical characteristics of insecticidal material in purified fractions derived from strain 5767 have been studied. There may be more than one insecticidally-active ingredient in this material which is distinct from the CryIIIA delta-endotoxin. At least one component of the insecticidal material derived from *B thuringiensis* strain 5767 is proteinaceous. The active ingredient(s) is (are):

macromolecular (not dialysable);
precipitated by ammonium sulphate;
reduced in efficacy by boiling;
reduced in efficacy by protease treatment;
not lipid;
associated with both protein and carbohydrate;
sometimes aggregated.

We further provide novel insecticidal compositions containing an insecticidal protein produced by strain JHCC 5767, and a process for protecting plants from insect attack which comprises exposing the insects to insecticidal protein produced by strain JHCC 5767. We further provide a method of isolating a novel insecticidal protein gene from said strain JHCC 5767.

*B thuringiensis* strain JHCC 5767 may be prepared in any quantity required by fermenting a sample of NCIMB 40533 obtained from the National Collections of Industrial and Marine Bacteria under suitable conditions in an appropriate medium. Such conditions and media are well known to the art. The media will, for example, generally contain a nitrogen source (e.g. fish protein) and a carbohydrate source such as starch. Suitable conditions include a temperature in the range of 15°-30° C., and an appropriately neutral pH. Fermentation may be conveniently carried out in batches, typically for periods of 3-5 days (until complete sporulation is observed).

Insecticidal compositions according to the invention may be obtained from the fermentation liquor by concentration, for example by centrifugation or filtration followed by addition of any desired and appropriate formulating agents. Formulating agents which may be useful include for example surface active agents (e.g. wetting agents), solid diluents, dispersing agents and UV stabilisers. If desired, solid formulations may be prepared by known methods.

The process of the invention is generally carried out by treating (e.g. spraying) plants infested or liable to infestation by insects with insecticidal compositions as described above diluted with a diluent such as water. The effective agent is insecticidal protein; if desired this may be applied to the plants independently of the sporulated bacterial culture that produced it. Separation of the protein from the bacterial lysate is however generally not necessary.

Larvae which may be combatted by the process of the invention include Diabrotica species such as those shown in Table 2 below.

TABLE 2

| Common Name | Latin Name |
|---|---|
| Western Corn Rootworm | *Diabrotica virgifera virgifera* |
| Southern Corn Rootworm | *Diabrotica undecimpunctata howardi* |
| Northern Corn Rootworm | *Diabrotica barberi* |
| Mexican Corn Rootworm | *Diabrotica virgifera zea* |
| Banded Cucumber Beetle | *Diabrotica balteata* |
| Western Spotted | *Diabrotica undecimpunctata* |

TABLE 2-continued

| Common Name | Latin Name |
|---|---|
| Cucumber Beetle | *undecimpunctata* |

The process of the invention may be used to protect a wide variety of plants, including maize (corn), potato, tomato, cotton, tobacco and cucurbits.

One method of carrying out the process of the invention is to arrange for the plant susceptible to insect attack to produce the insecticidal protein in situ. This is done by cloning an insecticidal protein gene from strain JHCC 5767 (NCIMB 40533), providing it with a suitable promoter (for example the CaMV35S promoter) which will cause expression of the gene in plants, and transforming the plant by known methods (e.g. bombardment of maize suspension cells with DNA-coated particles).

One or more insecticidal protein genes may be cloned from strain JHCC 5767 by the method of "reverse-cloning", used when there is no suitable DNA probe immediately available. The insecticidally-active protein produced by strain JHCC 5767 is purified to homogeneity and its N-terminal amino acid sequence is determined. This amino acid sequence information is then used to design a degenerate oligonucleotide DNA probe for use in screening a genomic library prepared from *B thuringiensis* strain JHCC 5767. The relevant gene may then be cloned by known means.

The following Examples illustrate the invention.

EXAMPLE 1

Isolation of *B thuringiensis* strain JHCC 5767.

Soil samples were diluted by placing 5.0 g of the sample into 45 ml of 0.5% peptone to give a $10^{-1}$ dilution prior to emulsification. The sample was then heated to 60° C. for 10 minutes in a water bath. Sequential dilutions were then made prior to plating 0.1 ml of the $10^{-3}$ and $10^{-5}$ dilutions onto *B. cereus* selective agar plates (*Bacillus cereus* agar base, Oxoid) and esculin agar plates (in g/litre of H2O: esculin 1.0; ferric citrate 0.5; peptone 10; NaCl 5; Oxoid agar 10). The plated samples were incubated at 30° C. for 5 days. Slides were made of potential *B. thuringiensis* colonies, stained according to Smirnoff's procedure and examined microscopically at 1000× magnification for the presence of stained, parasporal crystals.

Crystal-positive colonies were streaked onto L agar (10 g tryptone, 10 g yeast extract, 5 g NaCl, 10 g agar per litre) in order to ensure a pure culture, and incubated at 30° C. Purified colonies were incubated overnight in L broth; after incubation an equal volume of 80% sterile glycerol was added prior to storage at −70° C.

EXAMPLE 2

Propagation of *B thuringiensis* strain JHCC 5767 on CRL 1 solid media.

Inoculum was transferred from a glycerol storage vial onto an L agar plate to check for purity. A representative sweep of colonies was then used to inoculate 5 ml of L broth (10 g tryptone, 10 g yeast extract, 5 g NaCl per litre) prior to incubation with shaking at 30° C. for 3–5 hours. One millilitre of this culture was then used to inoculate a preparative (210 mm×210 mm) Petri plate containing 300 ml of CRL 1 medium agar (in g or ml/litre of water: nutrient broth 8; glucose 6; yeast extract 5; xylose 0.5; cotton seed flour extract 30 ml; corn steep liquor 3.2 ml; Mary Mendel's salt mixture 1 ml; Oxoid agar 15). Mary Mendel's salt mixture is:

| Mary Mendel's Salts | |
|---|---|
| Distilled Water | 495 ml |
| HCl conc. | 5 ml |
| $FeSO_4$ | 2.5 g |
| $MnSO_4$, $H_2O$ or $MnCl_2.4H_2O$ | 0.98 g |
| $ZnCl_2$ or $ZNSO_4.4H2_O$ | 1.76 g |

Cultures were incubated for 5 days at 30° C. The cells, spores and crystals were then harvested by scraping confluent growth from the agar surface prior to freeze-drying.

EXAMPLE 3

Propagation of *B thuringiensis* strain JHCC 5767 in CRL 1 liquid culture.

Inoculum was transferred from a glycerol storage vial to a 250 ml Erylenmeyer flask containing 100 ml of CRL 1 medium (in g or ml/litre of water: nutrient broth 8; glucose 6; yeast extract 5; xylose 0.5; cotton seed flour extract 30 ml; corn steep liquor 3.2 ml; Mary Mendel's salt mixture 1 ml) and incubated with agitation at 30° C. and 3400 rpm. After 24 hours, the entire 100 ml was used to inoculate 1 litre of the same medium in a 2L flask; this was incubated with agitation for 5 days at 30° C. The cells, spores and crystals were then harvested by centrifugation and acetone precipitated using the Dulmage method.

EXAMPLE 4

Large Scale fermentation of *B thuringiensis* strain JHCC 4279 in TSB medium.

Inoculum was transferred from a glycerol storage vial to an L-agar plate.

After overnight incubation at 30° C. an inoculum was transferred from the plate to a baffle flask containing 200 ml Nutrient Broth (Oxoid) prior to incubation with shaking (200 rpm) for 10 h at 28° C. The inoculum was transferred to a 2 litre seed Fermenter as a 1:100 dilution into the media described below; culture growth was allowed to proceed for 10 $^h$ at 28° C. The entire 2 litre culture was used to seed a BioStat E fermenter containing 11 litres of Arkasoy medium (The British Arkady Co, Ltd), supplemented with 40 g/litre glucose and pre-warmed to 30° C. Fermentation was allowed to proceed at 30° C., pH7.0±0.02, stirring at 800 rpm, with a dissolved oxygen ($PO_2$) setting of 70. PPG 2025 antifoam (BDH) was used at a 3:90 setting. The developmental stage of the culture was monitored every 3 hours prior to harvest at 90–100% sporulation. Harvested cells were collected by centrifugation and washed twice in cold, sterile distilled $H_2O$ prior to lyophilisation. 10 g aliquots of lyophilised fermentation product were stored in sterile containers at −70° C.

EXAMPLE 5

Formulation.

Upon completion of the fermentation, JHCC 5767 bacteria are harvested by first separating the *B thuringiensis* spores and crystals from the fermentation broth as described in Example 2. The recovered spores and crystals are resuspended in 100 ml of water and formulated into a liquid concentrate by adding 4.9 g of Morwet D-425 (dispersing agent), 4.9 g of Veegum HV (suspending agent), 4.9 ml of Tween 80 (wetting agent) and 24.4 ml of Sorbo (anti-freezing agent). Each ingredient is added separately in order stated above. The product is kept at 4° C. prior to use.

EXAMPLE 6

Partial purification of insecticidal protein(s) from *B thuringiensis* strain 5767.

Up to 9 g of lyophilised, sporulated culture was acetone washed as follows: 3 g aliquots were resuspended in 25 ml 4% lactose and stirred on ice prior to the gradual addition of 125 ml cold acetone over a period of 5 minutes. The solution was stirred for 30 minutes on ice, then left to stand for 15 minutes without stirring prior to filtration through a Whatman No 1 filter paper using a Buchler funnel. The powder was again resuspended in 80 ml cold acetone and filtered as above. This washing step was repeated a second time prior to placing the powder in a glass Petri dish covered with filter paper then drying overnight in a fume cupboard.

Washed power was then homogenised in 150 ml 100 mM Tris, pH 8.0, sonicated with 5 bursts of 20 seconds (30 seconds between bursts) at an amplitude of 10–14 microns, and incubated for 2 hours at 37° C. prior to centrifugation at 100,000×g for 60 min at 4° C. The resulting extract was precipitated with 70% ammonium sulphate (AS).

The resuspended AS pellet was then further purified by gel filtration followed by ion exchange chromatography, or dialysed into a buffer suitable for ion exchange chromatography followed by gel filtration. In the former method, material was applied directly to Superdex gel filtration columns and resultant fractions pooled based on similarities of SDS-PAGE patterns, usually forming 3 pools. Pooled fractions were then subjected to Mono Q ion exchange chromatography. Proteins were eluted from the MonoQ column with O-400, O-600, or O-700 mM Nacl gradients followed by a final 1M NaCl elution step. Purified or partially-pure protein fractions were desalted by dialysis into 10 mM Tris pH 8.0 prior to further analysis in insect bioassays. These protocols produce purified samples consisting of 1–3 protein bands ranging in size from 35 to 44 kilodaltons as judged by SDS-PAGE.

EXAMPLE 7

The insecticidal activity of strain JHCC 5767.

For tests on first instar larvae of Western Corn Rootworm (*Diabrotica virgifera virgifera*), purified fractions in 10 mM Tris pH 8.0, or freeze-dried spores and crystals, were mixed with sterile water and a sterile sucrose solution to give the required treatment rate in parts per million and a final 2.5% sucrose concentration. The solubilised spore/crystal (treatment) mixture was homogeneously dispersed by sonication in a water bath sonicator for 5 minutes. The treatment was then vortexed and applied as 0.075 ml of solution to a 1.5 cm disk cut from "Teri towels" (Kimberly Clark product #34770). One test consisted of 5–10 Teri towel disks with applied treatment, each held in a separate Falcon (TM) test dish prior to infestation with 5 first instar larvae per dish. Tests were placed in a closed styrofoam (polystrene) box with a moistened Teri towel placed in the bottom as an humidity source; the box was incubated in a constant-temperature room at 78°–80° F. for 4 or 5 days after treatment (DAT) prior to evaluation of the bioassay. The condition inside the Styrofoam box were 74°–76° F. and 80% relative humidity. Tests were evaluated using a dissecting microsope. For tests on 1-day-old Colorado Potato Beetle (*Leptinotarsa decemlineata*) larvae, freeze-dried spores and crystals were mixed with sterile water and presented on potato leaves dipped in this suspension.

Table 3 shows the insecticidal activity of various protein fractions from *B thuringiensis* strain JHCC 5767 and their immunological relatedness to CryIIIa delta-endotoxin (66 kD protein). The following abbreviations are used in the Table: Col. Pot. Beetle=*Leptinotarsa decimlineata*; W. Corn Rootworm=*Diabrotica virgifera virgifera*; *=active; **=very active; —=no activity; ?=ambiguous result; ND=not determined; kD=kilodalton; NaBr extr.=extracts prepared according to Carroll J et al, 1989, Biochem J, 261:99–105.

The data in Table 3 indicate that with increasing purification, the material larvicidal to Colorado Potato Beetle can be separated from the material insecticidal to Western Corn Rootworm.

TABLE 3

Insecticidal activity of various protein fractions from *B thuringiensis* strain JHCC 5767 and immunological relatedness to cryIIIa delta-endotoxin (66 kD protein).

| Prep8 Purified Fraction: | Activity vs Col. Pot. Beetle | Activity vs W. Corn Rootworm | Antigenic reaction vs anti-66kD antibody |
|---|---|---|---|
| Tris extract | — | ** | v. faint |
| CAPS extract | ? | ** | 55 & 66kd |
| NaBr extr. | * | * | 55 & 66kd |
| Tris Sol | | | |
| NaBr extr. | — | — | 55 & 66kd & lower MW |
| CAPS I Sol | | | |
| CAPS I | — | — | 55 & 66kd |
| Superdex 2 | | | |
| NaBr extr. | * | — | 55 & 66kd |
| CAPS II Sol | | | |
| Tris Superdex | | | |
| S1 | — | * | — |
| S2 | — | * | — |
| S3 | ? | ? | — |
| S4 | — | ? | — |
| S5 | — | — | — |
| Tris Mono Q | | | |
| M1 | ND | — | — |
| M2 | ND | — | — |
| M3 | ND | — | — |
| M4 | ND | — | — |
| M5 | ND | — | — |
| M6 | ND | — | — |
| M7 | ND | — | — |

Table 4 shows the larvacidal activity of Superdex-purified fractions on Western Corn Rootworm, and the effect of boiling the purified material (PPM=parts per million; DAT=Days after treatment; boiled samples were boiled for 5 minutes; JHCC 5767 powder was the starting material for the purification; Tris/Sucrose non-treatment control is 10 mM Tris pH8.0 in sterile sucrose).

TABLE 4

Larvacidial activity of Superdex-purified fractions from *B thuringieusis* strain 5767.

| Prep11 Sample: | Treatment Concentration: (PPM) | Western Corn Rootworm % Mortality at: 4DAT | 5DAT |
|---|---|---|---|
| S1 | 102 | 68 | 98 |
| S1-BOILED | 102 | 33 | 63 |
| S2 | 100 | 24 | 80 |
| S2-BOILED | 100 | 18 | 52 |

TABLE 4-continued

Larvacidial activity of Superdex-purified fractions from *B thuringieusis* strain 5767.

| Prep11 Sample: | Treatment Concentration: (PPM) | Western Corn Rootworm % Mortality at: 4DAT | 5DAT |
|---|---|---|---|
| S3 | 100 | 10 | 20 |
| S3-BOILED | 100 | 4 | 16 |
| JHCC 5767 POWDER | 4800 | 56 | 88 |
| TRIS/SUCROSE | — | 6 | 6 |

As shown in Table 4, Superdex fractions S1 and S2 (prepared as described in Example 6 but without the acetone-wash or 0–70% AS precipitation) were insecticidal to Western Corn Rootwarm (WCR) four or five days after treatment at a concentration of 100 parts per million (ppm). The starting material, *B thuringiensis* strain 5767, was presented at a treatment concentration of 4800; this indicates the efficacy of the purification method. The fact that insecticidal activity is reduced by boiling suggests that at least a component of the active ingredient(s) is proteinaceous.

The S1 fractions (Table 3, Table 4) were usually characterised by three major protein bands ranging in size from 35 to 44 kilodaltons as judged by SDS-PAGE. S1 fractions from Table 4 were subjected to further purification by ion exchange chromatography. This resulted in apparent single-band purity with protein band eluting at the high-salt end of the MonoQ gradient.

EXAMPLE 8

Larvacidal efficacy of both Superdex-purified and MonoQ-purified fractions a Western Corn Rootworm.

This Example illustrates the efficacy of both gel filtration (Superdex) and ion exchange chromatography (MonoQ) in purification of insecticidal fractions from strain JHCC 5767.

Insect bioassays were performed as described in Example 7. JHCC 5767 partially-purified fractions were prepared as described in Example 7 for the Superdex material. For MonoQ fractions, dialysed Tris extract was applied to the ion exchange column; fractions were eluted with a 0–400 mM NaCl gradient.

TABLE 5

Larvacidal activity of Superdex and MonoQ-purified fractions from *B thuringiensis* strain 5767.

| Prep12 Sample: | Treatment Concentration: (PPM) | Western Corn Rootworm % Mortality at: 4DAT | 5DAT |
|---|---|---|---|
| S1 | 50 | 48 | 68 |
| S2 | 50 | 8 | 22 |
| S3 | 50 | 16 | 24 |
| S4 | 50 | 16 | 18 |
| M-PASS | 279 | 100 | 100 |
| M1 | 350 | 16 | 50 |
| M2 | 126 | 8 | 34 |
| M3 | 207 | 26 | 44 |
| M4 | 162 | 24 | 46 |
| M5 | 252 | 36 | 72 |
| JHCC 5767 powder | 4800 | 76 | 96 |

TABLE 5-continued

Larvacidal activity of Superdex and MonoQ-purified fractions from *B thuringiensis* strain 5767.

| Prep12 Sample: | Treatment Concentration: (PPM) | Western Corn Rootworm % Mortality at: 4DAT | 5DAT |
|---|---|---|---|
| Tris/sucrose | — | 4 | 6 |

Tris/sucrose non-treatment control is 10 mM Tris pH 8.0 in 2.5% sterile sucrose; S1–S4 = Superdex fractions; M1–M5 = MonoQ fractions eluted from low (M1) to high (m5) NaCl concentrations; M-PASS = MonoQ "pass-through" material which did not bind to the column and eluted prior to starting the NaCl-gradient; JHCC 5767 powder was the starting material for the purification; PPM = parts per million; DAT = days after treatment.

Results in Table 5 show that the S1 Superdex-purified material is highly insecticidal. Results from MonoQ fractions (Table 5) indicate that insecticidal material eluted from the high-salt end of the gradient (eg M5) and also with the "pass through"0 material that did not bind to the ion exchange column. The high insecticidal activity of purified fractions at low treatment concentrations compared to the JHCC 5767 powder starting material indicate the efficacy of both purification procedures.

EXAMPLE 9

Effect of 0–70% ammonium sulphate precipitation and Superdex-purification following MonoQ-purification on insecticidal activity of JHCC 5767 purified fractions.

This Example illustrates the the effect of gel filtration following ion exchange chromatography on insecticidal activity.

Insect bioassays were performed as described in Example 7. Tris-extracted material was prepared as described in Example 7 then subjected to ammonium sulphate (AS) precipitation. The solubilised 0–70% AS fraction was dialysed, then subjected to MonoQ-purification. MonoQ fractions 27–30 (from the "high-salt" portion of the elution gradient) were further purified by gel filtration on a Superdex column. Insect bioassay results for this purification (Table 6) show that most of the larvacidal activity resides in the 0–70% AS fraction.

TABLE 6

Larvacidal activity of fractions derived from ammonium sulphate precipitation, and of highly-purified protein fractions.

| Prep21 Sample: | Treatment Concentration: (PPM) | Western Corn Rootworm % Mortality at: 3DAT | 4DAT | 5DAT |
|---|---|---|---|---|
| Tris extract | 50 | 8 | 16 | 42 |
| 0–70% AS | 50 | 54 | 96 | 100 |
| 70–80% AS | 50 | 4 | 4 | 6 |
| | 200 | 8 | 32 | 54 |
| 80% AS | 50 | 4 | 4 | 6 |
| | 200 | 4 | 4 | 22 |
| M27-30 | 110 | 10 | 16 | 30 |
| S9* | 50 | 2 | 2 | 4 |
| S10* | 41 | 2 | 4 | 6 |
| S11 | 45 | 12 | 20 | 26 |
| S12 | 20 | 6 | 18 | 38 |
| S13 | 34 | 4 | 4 | 6 |
| S14 | 43 | 50 | 90 | 100 |
| S17 | 18 | 4 | 8 | 14 |
| S18 | 29 | 0 | 2 | 16 |
| S19 | 14 | 4 | 10 | 10 |
| JHCC 5767 powder | 4800 | 56 | 88 | 96 |
| Tris control | — | 3 | 7 | 14 |

TABLE 6-continued

Larvacidal activity of fractions derived from ammonium sulphate precipitation, and of highly-purified protein fractions.

| Prep21 Sample: | Treatment Concentration: (PPM) | Western Corn Rootworm % Mortality at: 3DAT | 4DAT | 5DAT |
|---|---|---|---|---|
| (ave) | | | | |

AS = ammonium sulphate; fractions of apparent single-band purity on SDS-PAGE; JHCC 5767 powder = starting material for the purification; M = MonoQ; S = Superdex; Tris & AS samples were tested separately; PPM = parts per million; DAT = days after treatment.

Results in Table 6 also show that a pooled fraction from the "high salt" portion of the MonoQ elution gradient can be further resolved by gel filtration into fractions of varying insecticidal activity. As indicated in Table 6, seven of the nine Superdex fractions were of apparent single-band purity and ranged in size from 35–44 kilodaltons as judged by SDS-PAGE. These results indicate that apparently pure protein fractions consisting of a single band of 35–40 kilodaltons (eg S14) can be insecticidal to Western Corn Rootworm.

EXAMPLE 10

Specific activity increases following purification.

This Example illustrates the purification efficacy of the gel-filtration followed by ion exchange chromatography protocol.

Insect bioassays against Western Corn Rootworm were performed as described in Example 7. Purified material was prepared according to the protocol in Example 3. Results shown in Table 7 indicate that an approximately 12-fold increase in specific (insecticidal) activity was achieved by subjecting the initial pooled Superdex fractions (approximately equivalent to the S1 Superdex fractions in Tables 4 and 5) to ion exchange chromatography. In this experiment MonoQ fraction I, which was eluted with the final 1M NaCl step then dialysed into 10 mM Tris pH 8.0 prior to insect bioassay, represented an 11.9-fold increase in specific activity as compared to the Superdex A fraction loaded onto the MonoQ column.

TABLE 7

SPECIFIC ACTIVITY ESTIMATIONS AGAINST WESTERN CORN ROOTWORM

| Prep29 Sample | Rate (PPM) | % Mortality at 5DAT* | Protein (mg) | Specific Activity | Total Activity |
|---|---|---|---|---|---|
| Superdex A | 56 | 28 | 0.625 | 0.46 | 290 |
| MonoQ | | | | | |
| -A | 41 | 0 | 0.068 | 0 | 0 |
| -B | 78 | 10 | 0.390 | 0.13 | 50 |
| -C | 72 | 2 | 0.160 | 0.028 | 4.44 |
| -D | 63 | 0 | 0.174 | 0 | 0 |
| -E | 97 | 0 | 0.38 | 0 | 0 |
| -F | 215 | 8 | 0.48 | 0.037 | 17.9 |
| | 50 | 4 | 0.48 | 0.080 | 38.4 |
| -G | 149 | 2 | 0.495 | 0.013 | 6.64 |
| | 50 | 2 | 0.495 | 0.040 | 19.80 |
| -H | 149 | 12 | 0.499 | 0.080 | 40.2 |
| | 50 | 2 | 0.499 | 0.040 | 20.0 |
| -I | 16 | 88 | 0.036 | 5.5 | 198. |

MonoQ fractions A–I were eluted with increasing concentrations of NaCl: A–H represent the 0–400 mM NaCl gradient; I is the fraction eluted with the final 1M NaCl step. Rate = Treatment concentration in parts per million (PPM); DAT = Days after treatment;

Control mortality has been subtracted.

EXAMPLE 11

Carbohydrate and protein content of purified, insecticidally-active fractions from *B thuringiensis* strain 5767.

This Example concerns an analysis of carbohydrate content and the effect of boiling and protease treatment on purified fractions insecticidal to Western Corn Rootworm.

Insect bioassays were performed as described in Example 7. Purified insecticidal fractions were prepared according to the protocol in Example 3. Carbohydrate content was estimated by acid hydrolysis followed by "total sugar" measurement using phenol/cysteine/sulphuric acid; glycogen (1mg/ml) was used as a standard. Measured optical density values were identical±cysteine, indicating that glucose was unlikely to be a major sugar in the carbohydrate.

Insect bioassay results are shown in Table 8. These data indicate that insecticidal activity was reduced by boiling, and by protease treatment, for purified fractions SA-M4, SB-M4 and SB-M5. This suggests that the insecticidally-active ingredient is, at least in part, proteinaceous.

Results of the carbohydrate analysis of these fractions are also shown in Table 8. These results, which are consistent with those from other experiments, indicate that high carbohydrate levels (>1 mg) are sometimes, but not always, associated with insecticidal activity,

TABLE 8

Determination of carbohydrate content, effect of boiling and protease treatment on purified, insecticidally-active fractions.

| Prep33 Sample | CHO content (mg) | Treatment conc. (PPM) | Western Corn Rootworm % Mortality: 5DAT | 5DAT + boil | 5DAT + protease |
|---|---|---|---|---|---|
| 70% AS | ND | 50 | 74 | 60 | 68 |
| Superdex SA | ND | 37 | 42 | ND | ND |
| Superdex SB | ND | 90 | 91 | ND | ND |
| Superdex SC | ND | 10 | 16 | ND | ND |
| MonoQ | | | | | |
| SA-M-PASS | 2.8 | 14 | 92 | 94 | 98 |
| SA-M4 | 0.3 | 248 | 44 | 10 | 26 |
| SA-M5 | 1.1 | 29 | 70 | 68 | 74 |
| SB-M-PASS | 0.4 | 9 | 34 | 44 | 29 |
| SB-M4 | 0.3 | 360 | 71 | 24 | 14 |
| SB-M5 | 1.25 | 56 | 82 | 68 | 52 |

CHO = carbohydrate; PPM = parts per million; ND = not determined; DAT = days after treatment; + boil = 10 minutes boil; + protease = Pronase e, thermolysin, and proteinase K each at a final concentration of 30 μg/ml extract, incubated for 2 hours at 37° C. (NB: proteases alone are inactive in the insect bioasay); 70% AS = re-suspended ammonium sulphate pellet; SA = initial Superdex pooled fractions (similar to S1 in Tables 4 & 5); SB = adjacent pooled Superdex fractions; M-PASS = MonoQ pass-through material which did not bind to the column and eluted prior to starting the NaCl-gradient; SA-M4, SA-M5, SB-M4 and SB-M5 are the insecticidally active fractions from the "high salt" portion of the Monoo elution gradient after application of Superdex fractions SA or SB.

EXAMPLE 12

Effect of lipid removal by acetone treatment.

This Example illustrates that lipid removal by acetone treatment of *B thuringiensis* strain 5657 lyophilised powder does not affect insecticidal activity.

Insect bioassays were performed as described in Example 7. Tris extracts and 0–70% suspended ammonium sulphate pellets were prepared as described in Example 6 except that one aliquot was acetone-washed as a *B thuringiensis* strain 5767 lyophilised powder (as described in Example 6) and one aliquot was acetone precipitated after the 0–70% ammonium sulphate step. As shown in Table 9, removal of lipid by acetone-treatment did not significantly reduce insecticidal efficacy of the treated fractions. Lipid tests were done by spotting 20 ml samples onto thin layer chromatography plates, spraying with phosphomolybdic acid, and heating to 110° C. prior to recording blue colour as an indicator of the presence of lipid. As shown in Table 9, acetone treatment of lyphilised *B thuringiensis* strain 5767 removes all detectable lipid from the 0–70% ammonium sulphate step onwards.

TABLE 9

Effect of lipid removal by acetone treatment.

| Sample | Western Corn Rootworm % Mortality at 5DAT | Detectable Lipid |
|---|---|---|
| Prep 26: | | |
| Tris extract | 93 | +/− |
| 0–70% AS | 96 | − |
| Prep 27: | | |
| Tris extract | 100 | + |
| Acetone-ppt. of 0–70% AS | 100 | +/− |

Prep 26 = Acetone washed strain 5767 powder;
Prep 27 = Untreated 5767 powder;
Insect bioassays on Preps 26 & 27 were done at the same time; samples were presented at a treatment concentration of 100 parts per million in the insect bioassays.

EXAMPLE 13

Amino acid sequence analysis of a purified insecticidal fraction.

The partial amino acid sequence of an apparently pure protein larvacidal to Western Corn Rootworm has been determined.

Sample S14, described in Example 9, was an apparently pure protein of approximately 35–41 kilodaltons in size as judged by SDS-page. An aliquot of the S14 material was analysed for N terminal amino acid sequence. Results are given below: the residue and corresponding one-letter-code are shown below the cycle number. Note that it was not possible to distinguish between glu and phe signals in cycle 11. (SEQ. ID NO: 1)

| 1 | 2 | 3 | 4 | 5 | 6 | 7 | 8 | 9 | 10 | 11 | 12 |
|---|---|---|---|---|---|---|---|---|---|---|---|
| X— | thr— | ser— | leu— | thr— | leu— | gln— | thr— | X— | X— | glu/phe— | ser |
| — | T | S | L | T | L | Q | T | — | — | E/F | S |

These data may be used to design a DNA probe enabling "reverse cloning" of the JHCC 5767-derived protein which is insecticidal to Western Corn Rootworm.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
Xaa Thr Ser Leu Thr Leu Gln Thr Xaa Xaa Xaa Ser
1               5                   10
```

AS = re-suspended 0–70% ammonium sulphate pellet after dialysis into 10 mM Tris pH 8.0;
DAT = days after treatment;
+ = positive (blue) lipid detection;
+/− = residual lipid detection;
− = no detectable lipid.

We claim:

1. An insecticidal protein produced by *Bacillus thuringiensis* strain JHCC 5767, said protein being larvacidal to Western Corn Rootworm, approximately 35 to 41 kilodaltons in size and having an N terminal amino acid sequence selected from the group consisting of XTSLTLQTXXES AND XTSLTLQTXXFS.

2. An insecticidal composition for combatting insects of the genus Diabrotica which comprises as active ingredient an insecticidal protein according to claim 1.

3. A process for protecting plants against attack by insects of the genus Diabrotica which comprises exposing the insects to an insecticidal protein according to claim 1.

* * * * *